(12) United States Patent
Nielsen et al.

(10) Patent No.: US 10,201,330 B2
(45) Date of Patent: Feb. 12, 2019

(54) GRAPHICAL VIRTUAL CONTROLS OF AN ULTRASOUND IMAGING SYSTEM

(71) Applicant: B-K Medical Aps, Herlev (DK)

(72) Inventors: Torben Svanberg Nielsen, Copenhagen (DK); Kaj Duncan, Stenlille (DK); Jesper Helleso Hansen, Copenhagen (DK); John Antol, Nahant, MA (US); Michael Leismann, Hvidovre (DK)

(73) Assignee: B-K Medical Aps, Herlev (DK)

( * ) Notice: Subject to any disclaimer, the term of this patent is extended or adjusted under 35 U.S.C. 154(b) by 167 days.

(21) Appl. No.: 15/126,084

(22) PCT Filed: Mar. 14, 2014

(86) PCT No.: PCT/IB2014/059836
§ 371 (c)(1),
(2) Date: Sep. 14, 2016

(87) PCT Pub. No.: WO2015/136336
PCT Pub. Date: Sep. 17, 2015

(65) Prior Publication Data
US 2017/0091404 A1 Mar. 30, 2017

(51) Int. Cl.
*A61B 8/00* (2006.01)
*A61B 8/08* (2006.01)
(Continued)

(52) U.S. Cl.
CPC .............. *A61B 8/54* (2013.01); *A61B 8/4405* (2013.01); *A61B 8/4483* (2013.01); *A61B 8/465* (2013.01);
(Continued)

(58) Field of Classification Search
CPC ....... A61B 8/54; A61B 8/4405; A61B 8/4483; A61B 8/465; G16H 40/63; G06F 3/04847; G06F 3/04886; G06F 19/321
See application file for complete search history.

(56) References Cited

U.S. PATENT DOCUMENTS

2004/0024384 A1 2/2004 Novak
2007/0142984 A1 7/2007 Ording et al.
(Continued)

FOREIGN PATENT DOCUMENTS

EP 2191776 A1 6/2010
EP 2702947 3/2014
WO 2013077291 A1 5/2013

OTHER PUBLICATIONS

International Search Report for PCT/IB2014/059836 published as WO2015/136336 A1 dated Sep. 17, 2015.

*Primary Examiner* — Angie M Badawi
(74) *Attorney, Agent, or Firm* — Anthony M. Del Zoppo, III; Daugherty & Del Zoppo, Co., LPA (57) ABSTRACT

A method includes receiving, at a console (132) of an ultrasound imaging system (102), a first signal indicative of actuation of a touch control (128) of a touch screen user interface (122) of the ultrasound imaging system, wherein the touch control is one of a plurality of different touch controls of the ultrasound imaging system. The method further includes identifying, with a processor of the ultrasound imaging system, the touch control from the plurality of different touch controls based on the first signal. The method further includes identifying, with the processor of the ultrasound imaging system, a graphic representation of the touch control based on the identification of the touch control. The method further includes visually displaying, (Continued)

with the processor of the ultrasound imaging system, the graphic representation on a display monitor concurrently with displaying an image.

20 Claims, 10 Drawing Sheets

(51) Int. Cl.
    *G06F 19/00*         (2018.01)
    *G16H 40/63*        (2018.01)
    *G06F 3/0484*      (2013.01)
    *G06F 3/0488*      (2013.01)

(52) U.S. Cl.
    CPC ............... *A61B 8/467* (2013.01); *A61B 8/52* (2013.01); *G06F 3/04847* (2013.01); *G06F 3/04886* (2013.01); *G06F 19/00* (2013.01); *G06F 19/321* (2013.01); *G16H 40/63* (2018.01)

(56) References Cited

U.S. PATENT DOCUMENTS

| | | | |
|---|---|---|---|
| 2011/0182137 A1* | 7/2011 | Ozaki | ...................... A61B 8/00 367/7 |
| 2012/0081299 A1* | 4/2012 | Xiao | ................ H04N 21/42224 345/173 |
| 2012/0232367 A1 | 9/2012 | Allegri et al. | |
| 2013/0120402 A1* | 5/2013 | Adams | ....................... G06F 9/44 345/473 |
| 2013/0197364 A1 | 8/2013 | Han | |

* cited by examiner

GRAPHICAL VIRTUAL CONTROLS OF AN ULTRASOUND IMAGING SYSTEM

RELATED APPLICATION

This application is a national filing of PCT application Serial No. PCT/IB2014/059836, filed Mar. 14, 2014, published as WO2015/136336 on Sep. 17, 2015. This application claims priority to PCT application Serial No. PCT/IB2014/059836, published as WO2015/136336 on Sep. 17, 2015.

TECHNICAL FIELD

The following generally relates to ultrasound imaging and more particular to displaying, on a display monitor, a virtual control or representation mimicking an active touch screen user interface control and operation thereof.

BACKGROUND

An ultrasound imaging system has included an ultrasound probe with a transducer, a console with an integrated or external display monitor, and a user interface. The transducer transmits an ultrasound signal into a field of view and receives echoes produced in response to the signal interacting with structure therein. The echoes are conveyed to the console and are processed, producing images of the scanned structure, which may be visually presented through the display monitor.

The display monitor may include a cathode ray tube (CRT), a liquid crystal display (LCD), a light emitting diode (LED) display, and/or other type of display. The display monitor has been a "dumb" monitor with no processor or processing capabilities and that is simply an output device that displays images and other information (e.g., transducer frequency, gain, etc.). The user interface has included a keyboard or keypad with mechanical depressable buttons and/or a flat touch screen area (e.g., LCD, CRT, etc.).

The display monitor has been placed in an upright vertical position so that the clinician can look at images and/or the other information displayed via the display monitor. The user interface has been placed in a generally horizontal position, approximately perpendicular to the upright vertical position. This arrangement is similar to that of a desktop computer monitor and corresponding keyboard. The user controls features such as gain, zoom, pans, etc. with the controls of the user interface.

Unfortunately, with such a user interface/display monitor arrangement, where the user interface includes a touch screen with a flat surface, it may not be readily easy for the user to locate and/or operate touch sensitive controls of the user interface while observing an image and/or patient. Rather, the user may have to look away from the image and/or patient and down at the user interface to find and/or operate the control, adding complexity and inefficiency to the procedure.

SUMMARY

Aspects of the application address the above matters, and others.

In one aspect, a method includes receiving, at a console of an ultrasound imaging system, a first signal indicative of actuation of a touch control of a touch screen user interface of the ultrasound imaging system, wherein the touch control is one of a plurality of different touch controls of the ultrasound imaging system. The method further includes identifying, with a processor of the ultrasound imaging system, the touch control from the plurality of different touch controls based on the first signal. The method further includes identifying, with the processor of the ultrasound imaging system, a graphic representation of the touch control based on the identification of the touch control. The method further includes visually displaying, with the processor of the ultrasound imaging system, the graphic representation on a display monitor concurrently with displaying an image.

In another aspect, an ultrasound imaging system includes a touch screen user interface including a touch panel active region with one or more touch controls, an ultrasound scanner console including a transducer controller, an echo processor and a display controller, and a display monitor, including at least two display regions. The display controller, in response to activation of one of the one or more touch controls, renders a virtual graphical control, which represents the one of the touch controls, in one of the display regions.

In another aspect, a computer readable storage medium is encoded with computer readable instructions which, when executed by a computer processor, cause the computer process to: display, in a display region of a display monitor of an ultrasound imaging system, a graphic that visually mimics an operation of a touch control of a touch screen user interface of the ultrasound imaging system, wherein the touch screen user interface and the display monitor are separate and distinct elements of the ultrasound imaging system.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
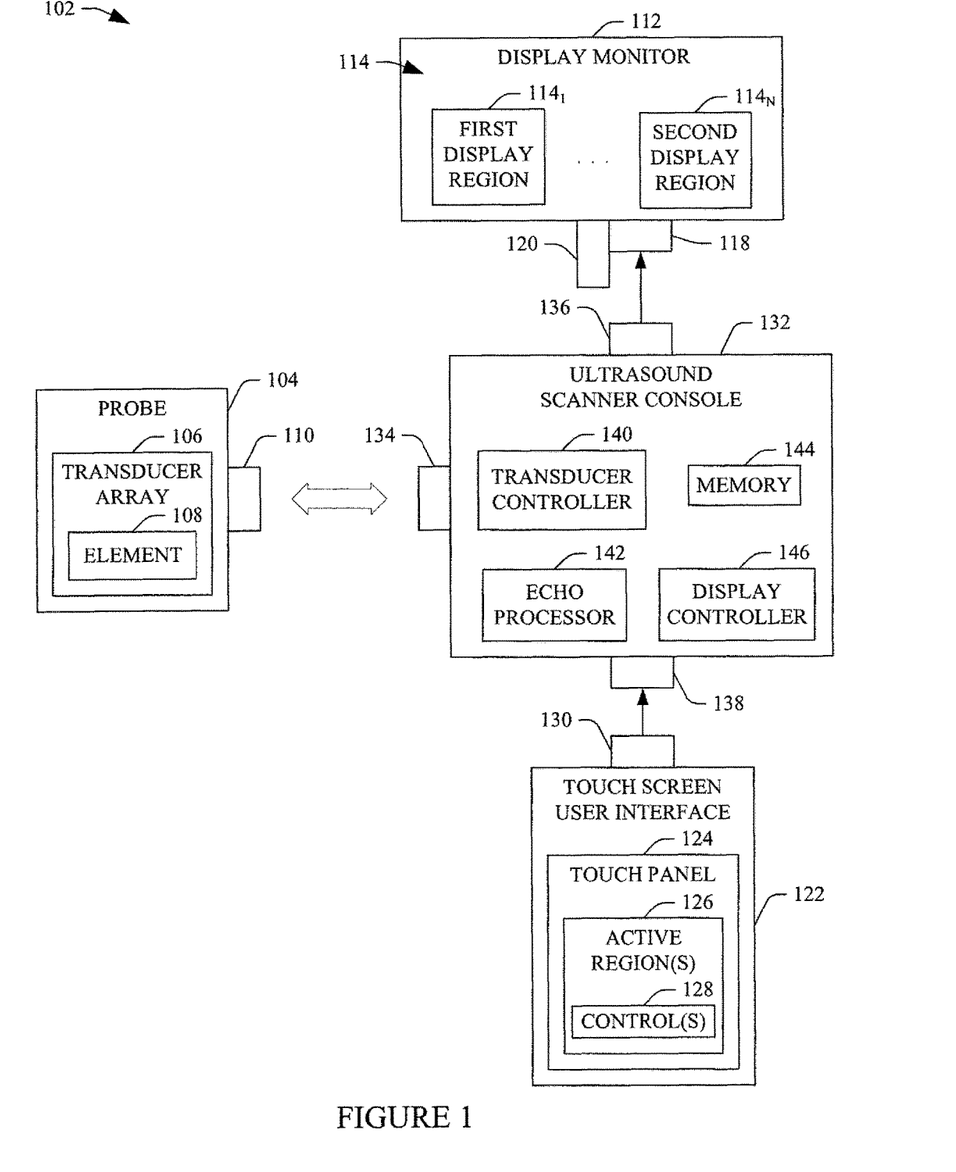
FIG. 1 schematically illustrates an example ultrasound imaging system that includes a touch screen user interface, a display monitor, and a console with a display controller that renders a virtual control on the display in response to activation and/or operation of a corresponding control of the touch screen user interface.

FIG. 1 schematically illustrates an ultrasound (US) imaging system 102.

The ultrasound imaging system 102 includes a probe 104 with a one-dimensional (1D) or two-dimensional (2D) transducer array 106 with at least one transducer element 108. Suitable array configurations include, but are not limited to, linear, curved (e.g., concave, convex, etc.), circular, etc., full populated or sparse, etc. The probe 104 further includes a console interface 110, which may include a connector (e.g., an electro-mechanical device for joining electrical circuits) and/or wireless transceiver.

The ultrasound imaging system 102 further includes a display monitor 112. The display monitor 112 can be a cathode ray tube (CRT), a liquid crystal display (LCD), a light emitting diode (LED), and/or other display monitor. The display monitor 112 includes a display area 114 with a multiple sub-display regions $114_1, \ldots, 114_N$, where N is a positive integer. The display monitor 122 further includes a console interface 110, which may include a connector (e.g., an electro-mechanical device for joining electrical circuits) and/or wireless receiver.

The display monitor 112 can be affixed to a support 120 (as shown in FIG. 1) such as a stand, a bracket, etc. that rests on or is affixed to a surface (e.g., a desk, a table, etc.) and holds the display monitor 112 in a generally upright vertical viewing position. In another instance, the support 120 can be a wall bracket that mounts to a wall, a ceiling, etc., thereby indirectly mounting the display monitor 112 thereto. Other supports are also contemplated herein. The support 120 may be configured to rotate, tilt, translate, and/or otherwise move, which selectively allows for spatially orienting the region 124.

The ultrasound imaging system 102 further includes a touch screen user interface 122. The touch screen user interface 122 includes a touch panel 124. At least a sub-portion of the touch panel 124 includes one or more active regions 126 with one or more touch sensitive control(s) 128 such as a time-gain control (TGC), a mode (e.g., 2D, 3D, 4D, etc.) selector control, a CINE control, a measurement control, a zoom control, a depth control, a focus control, etc. The touch panel 214 may include a resistive, a capacitive, an acoustic, an infrared, an optical, a piezoelectric, and/or other region. Furthermore, the touch panel 214 may include an LCD, thin film transistor (TFT) LCD, organic light-emitting diode (OLED), and/or other display.

The one or more controls 128, in one instance, are kept in a normally deactivate state, but are activatible. A deactivated control 128, when actuated by a gesture (e.g., a press, a swipe, a touch, etc.) on the control 128 with one or more fingers, a stylus, a glove, etc., transitions to an active state. An activate control 128, when operated, generates an electrical signal corresponding to the operation of the control 128. Generally, when a control 128 is active, one or more other non-active controls transition to a non-activatible state.

In a variation, one or more controls can be kept in a normally active state. In this variation, the normally active control may transition to a de-active state in response to activation of another control, a gesture over the control, an input signal including a control signal that deactivates the control, etc.

As an example of activation and operation, a gain control is activated by touching the control and then the gain is increased or decreased (i.e., operated) through the control through a predetermined gesture. For example, circling clockwise, sliding over in direction, etc. the gain control with a suitable object increases gain, and circling counter-clockwise, sliding in another direction, etc. over the gain control with the suitable object decreases gain. A reset control may be provided to quickly return on or more of the touch controls 128 to the initial or starting conditions. An active control can be configured to automatically transition back to a deactive state, e.g., in response to lapse of a pre-determined length of time of inactivity, activation of another control 126, on demand, etc.

Figure 2:
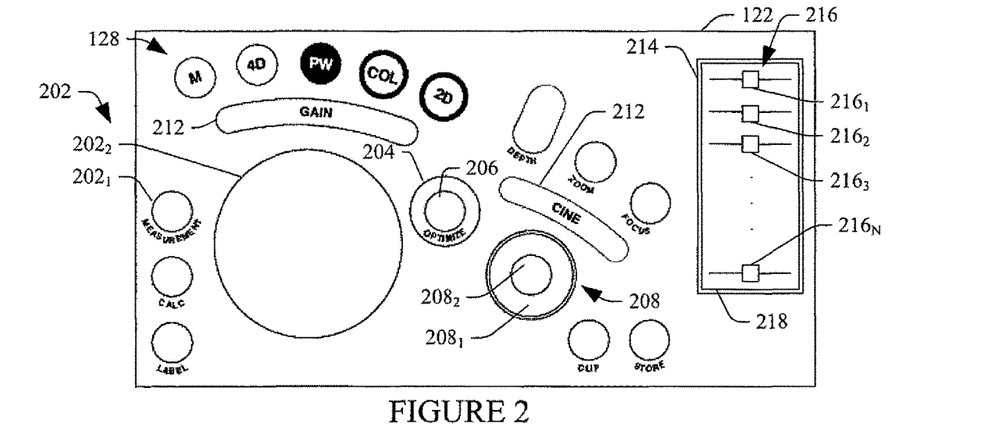
FIG. 2 illustrates an example of the touch screen user interface, including variously shaped controls.
Figure 3:
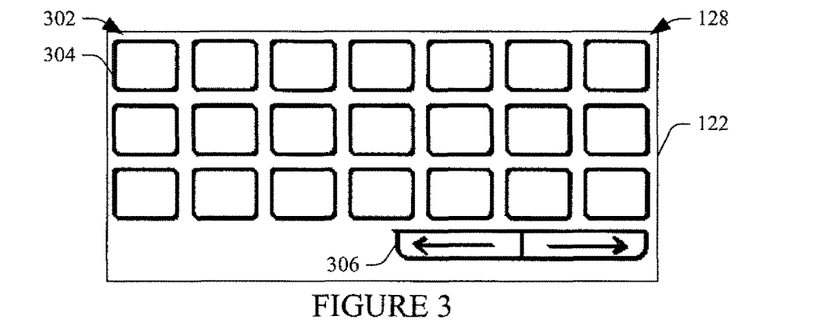
FIG. 3 illustrates another example of the touch screen user interface, including a 2D array of controls.
Figure 4:
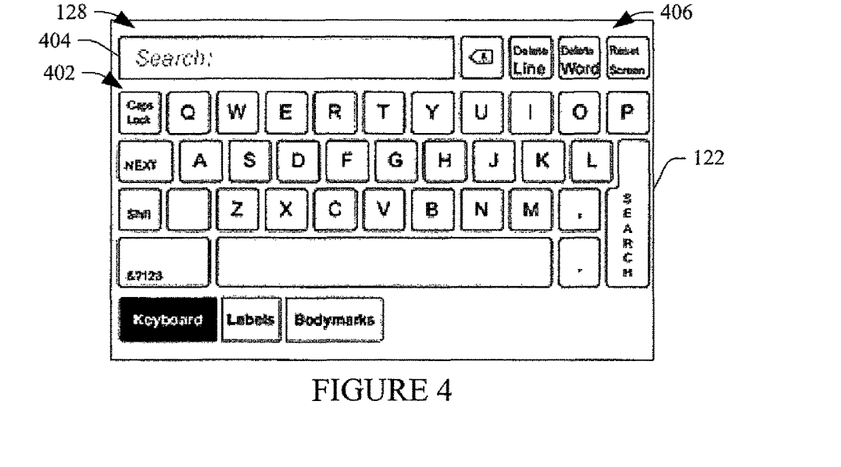
FIG. 4 illustrates yet another example of the touch screen user interface, including controls of a keyboard.

Briefly turning to FIGS. 2, 3 and 4, non-limiting examples of the touch screen user interface 122 are illustrated.

In FIG. 2, the controls 128 include circular shaped controls 202 including one control $202_1$ with one diameter and another control $202_2$ with a different larger diameter, a ring shape control 204 with a non-active area 206 in the hole of the ring, concentric controls 208 including one control $208_1$ surrounded by another control $208_1$, a rectangular control 210 with rounded edges, and curved rectangular controls 212 with rounded edges. A control 214 includes a plurality of touch activated slides $216_1, 216_2, 216_3, \ldots, 216_N$, collectively referred to herein as virtual slides 216, which reside in a recess 218 in the touch panel 124. Again, the controls 128 can be activated and used by pressing, tapping, swiping, etc.

Turning to FIG. 3, the controls 128 include a two-dimensional (2D) array 302 of rectangular controls 304 and other controls 306. In FIG. 4, the controls 128 include controls 402 of a computer keyboard as well as other controls 128, such as a search box 404, and custom configure controls 406. Another example touch screen user interface 122 includes a combination of FIGS. 2, 3 and/or 4, optionally with alternative and/or additional controls. Still other controls can also include physical mechanical controls such as a trackball, a track pad, etc. Other examples of touch screen controls are described in application Ser. No. 13/748,653, filed on Jan. 24, 2013, entitled "Ultrasound Imaging System," and assigned to B-K Medical Aps, which is incorporated herein by reference in its entirety.

Returning to FIG. 1, the touch screen user interface 122 may also include visual indicators (e.g., lights, etc.), audible indicators (e.g., speakers, etc.), tactile indicators (e.g., vibration, etc.), other controls (e.g., physical mechanical buttons, physical mechanical slides, physical mechanical rotary knobs, etc.), an image display region, etc. The touch screen user interface 122 further includes a console interface 130, which may include a connector (e.g., an electro-mechanical device for joining electrical circuits) and/or wireless transceiver.

The ultrasound imaging system 102 further includes an ultrasound scanner console 132. The console 132 includes a probe interface 134, a display monitor interface 136, and a touch screen user interface 138, which, respectively are complementary to the console interfaces 110, 118 and 130. For example, the probe interface 134 is complementary to the console interface 110 in that the probe interface 134 and the console interface 110 physically engage and provide an electrical pathway between the probe 104 and the ultrasound scanner console 132. For instance, the console interface 110 may include a female connector and the probe interface 134 may include a male connector, wherein the connectors physically engage and physically connect electrodes.

The ultrasound scanner console 132 further includes a transducer controller 140. The transducer controller 140 controls excitation of the at least one transducer element 108. The transducer controller 140 also controls detection of echoes with the at least one transducer element 108. In a variation, the excitation and detection can be through separate components such as transmit and receive circuitry. The console 132 further includes an echo processor 142 (e.g., microprocessor, central processing unit, etc.) that processes detected echoes. Such processing may include generating an image, estimating flow velocity, and/or processing. The ultrasound scanner console 132 further includes a physical memory device (memory) 144, which can be used to store ultrasound data.

A display controller 146 controls the information visually presented in at least one of the display regions 114 of the display monitor 112. By way of example, in one non-limiting instance, the display controller 146 renders an ultrasound image in at least one of the display regions 114. In another example, the display controller 146 renders a graphical representation of one of the controls 128 in at least one of the display regions 114. As described in greater detail below, for the latter, the display controller 146 identifies activation and/or operation of a touch control 128 and renders the graphical representation in the at least one of the display regions 114, where the graphical representation may include alpha-numeric information and/or graphics, shows a current value and/or any changes thereto, shows movement of the actual control, etc.

Generally, the graphical representation provides a virtual control of a touch control 128, on the display monitor 112, that mirrors or mimics the touch control 128 of the touch screen user interface 122 and operation of the touch control 128 through the touch screen user interface 122. The graphical representation shows in the display monitor 112, for example, where the user's finger (or other object) is located on the touch screen user interface 122 with respect to the control 128, thereby allowing the user to adjust a control 128 without looking at the control 128 on the touch screen user interface 122. In one instance, this provides a more intuitive adaptation of the touch controls, and may reduce complexity and inefficiency, relative to a configuration in which the display controller 146 does not render virtual controls on a display region of the display monitor 112.

Figure 5:
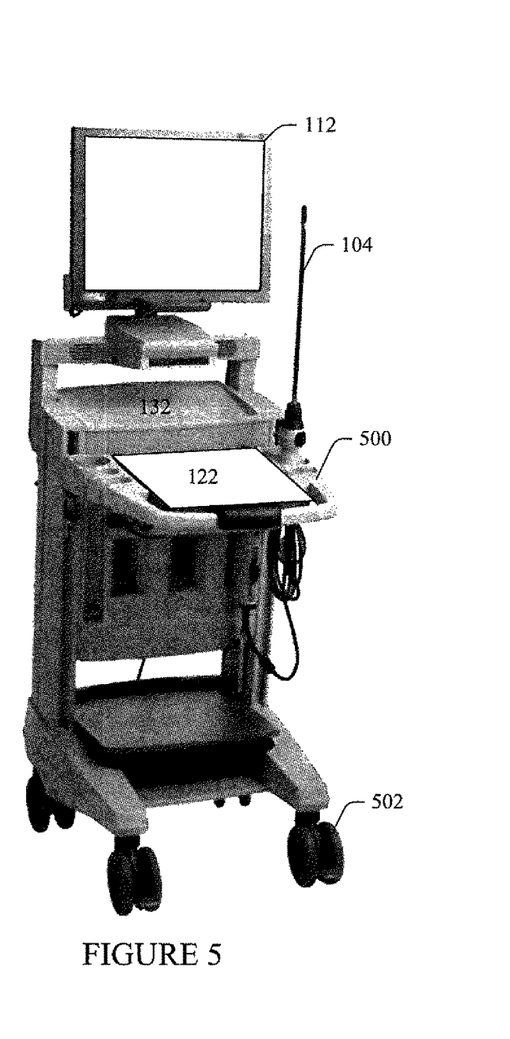
FIG. 5 illustrates an example of the ultrasound imaging system integrated as part of a mobile cart.
Figure 6:
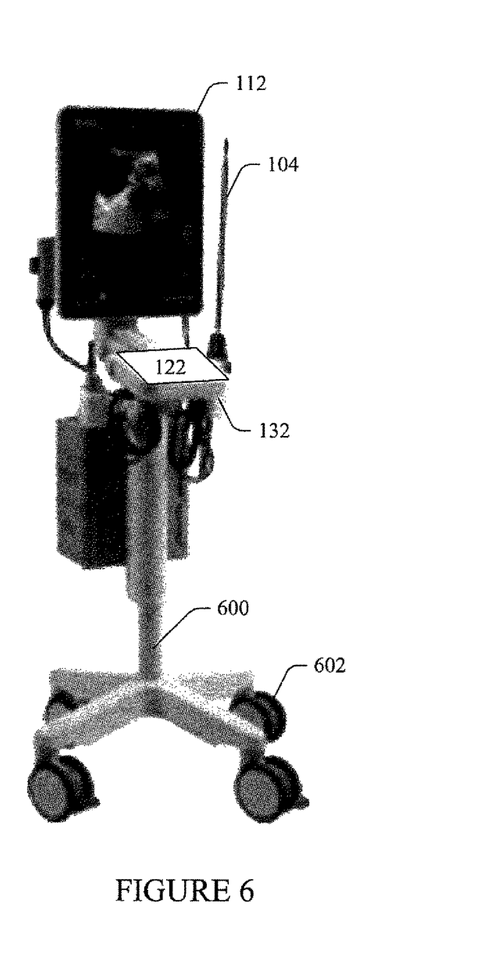
FIG. 6 illustrates another example of the ultrasound imaging system configuration integrated as part of a mobile cart.

FIGS. 5 and 6 illustrate non-limiting examples of the ultrasound imaging system 102. In the non-limiting examples, the display monitor 112, the touch screen user interface 122 and the ultrasound scanner console 132 are integrated and part of respective mobile carts 500 and 600, which include movers 502 and 602 such as wheels, casters, etc. In another configuration, the ultrasound imaging system 102 rests on a table, desk, etc., and does not include movers and is not integrated into a cart, is also contemplated herein. In this configuration, the ultrasound imaging system 102 may be portable in that a user can pick it up and carry it around or not. Further, the illustrated probe 104 does not limit the type of probe and shown for explanatory purposes.

Figure 7:
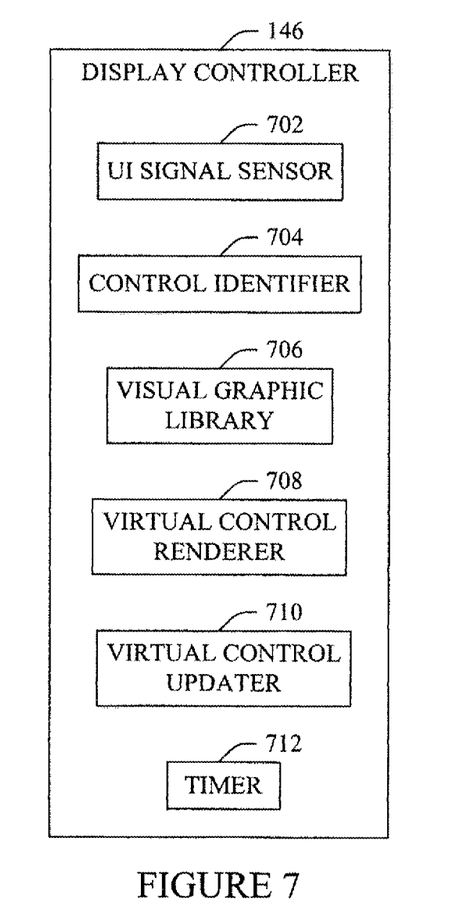
FIG. 7 schematically illustrates an example of the display controller of the ultrasound imaging system.

FIG. 7 schematically illustrates an example of the display controller 146.

The display controller 146 includes a user interface (US) signal sensor 702. The user interface signal sensor 702 senses when a touch control 128 of the touchscreen user interface 122 is activated and/or operated. By way of example, as described herein, activating a control 128 or operating the control 128 with an activate control 128 (e.g., through touch, etc.) invokes the control 128 to generate a signal, which is conveyed to the ultrasound scanner console 132. The user interface signal sensor 702 senses actuation and/or operation of a control 128 through this signal.

The display controller 146 further includes a control identifier 704, which, based on the sensed signal, determines which control 128 of the controls 128 generated the signal. Known and/or other approaches for identifying the control 128 can be used. For example, with a capacitive based touchscreen, when an object touches the control 128, a measureable change in capacitance occurs, and the location of the touch, and hence, the function corresponding to the control 128, can be determined.

The display controller 146 further includes visual graphic library 706, which can be stored in memory 144 and/or other memory. The visual graphic library 706, in the illustrated embodiment, includes instructions for generating a different graphic representation for each of the controls 128. In general, the graphic representation for a control 128 graphics mimics the appearance and/or operation of the control 128 on the touchscreen user interface 122.

The display controller 146 further includes virtual control renderer 708. The virtual control renderer 708 renders the graphic representation on the display region 114 not displaying the image. The virtual control renderer 708 also removes graphic representation from the display region 114. The display controller 146 further includes virtual control updater 710. The virtual control renderer 708 updates the graphic representation on the display region 114 in response to a signal indicating operation such as a change (e.g., an increase in gain) invoked by the control 128.

The display controller 146 further includes a timer 712. The timer 712 is invoked to start a count (increment or decrement) based on a pre-determined time duration in response to receiving a control activating signal, re-start the count in response to receiving a change in value signal for the activated control, start a count for another control in response to a control activating signal for another control, cease the count in response to the pre-determined time duration lapsed before another change in value signal is received.

The display controller 146 can be implemented by a computer processor (e.g., a microprocessor, a central processing unit, etc.) executing computer readable instructions stored on computer readable storage medium (which exclude transitory medium) such as hardware memory. Additionally or alternatively, at least one of the computer readable instructions is carried by a signal, a carrier wave and/or other transitory medium.

Figure 8:
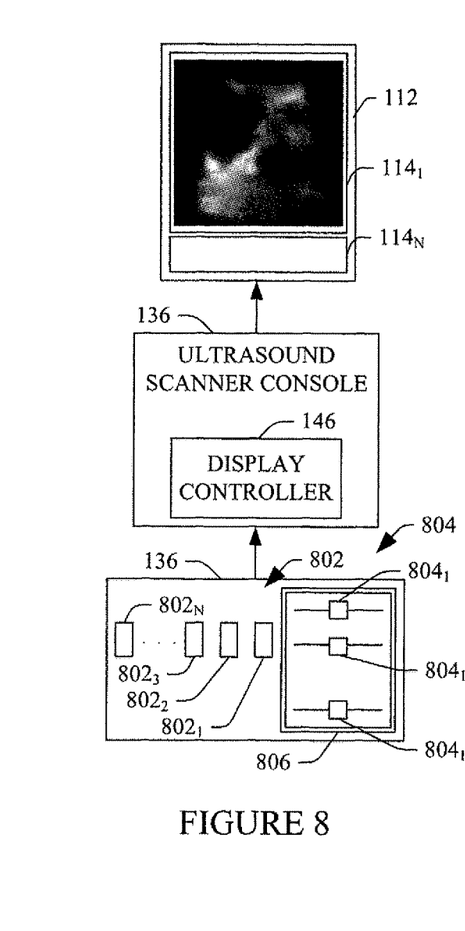
FIGS. 8-13 illustrate example operation of the display controller in connection with a first type of touch control.

FIGS. 8-13 illustrate example operation of the display controller;

In FIG. 8, the display region $114_1$ is used to display an image. The display region $114_N$ is used to display a virtual control. The touchscreen user interface 122 includes at least a set of controls $802_1$, $802_2$, $802_3$, . . . , $802_N$, collectively referred to herein as controls 802, and a set of controls $804_1$, $804_2$, . . . , $804_N$, collectively referred to herein as controls 804. The controls 804 are located in a region 806. All of the controls 802 and 804 are activatible.

Figure 9:
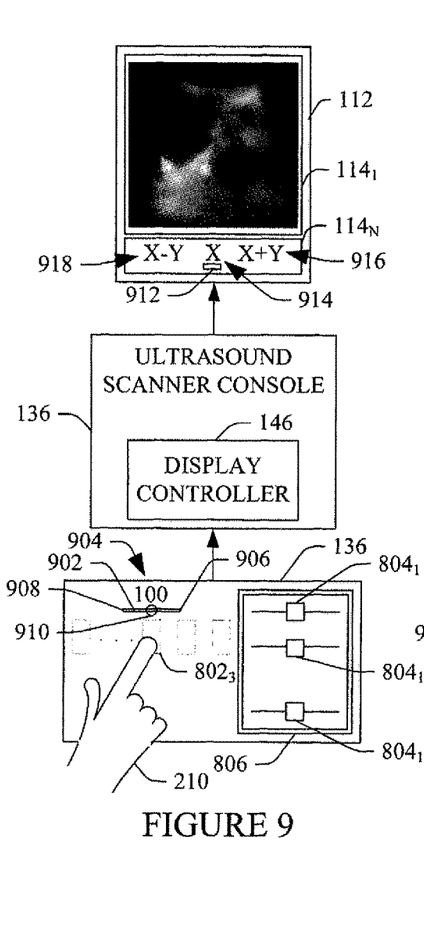

In FIG. 9, a user 210 actuates the control $802_3$ by pressing on the control $802_3$. In this example, in response thereto, the controls 802 and 804 transition to a state in which they cannot be activated, and a value line 902, a current value 904, end limits 906 and 908 (e.g., minimum and maximum values), and a value selector 910 are rendered above the control $802_3$, and a value selector 912, a current value 914, and minimum and maximum values 916 and 918 are rendered in the display region $114_N$. In this example, the selectors 910 and 920 are at a center position.

Figure 10:
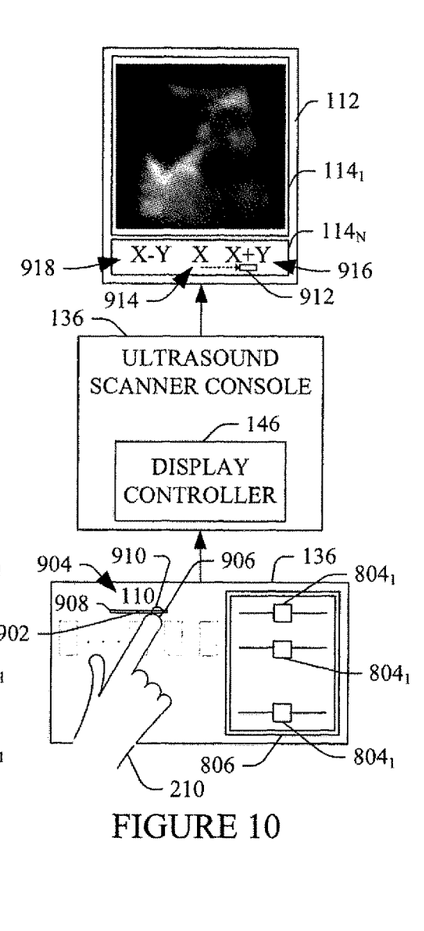
Figure 11:
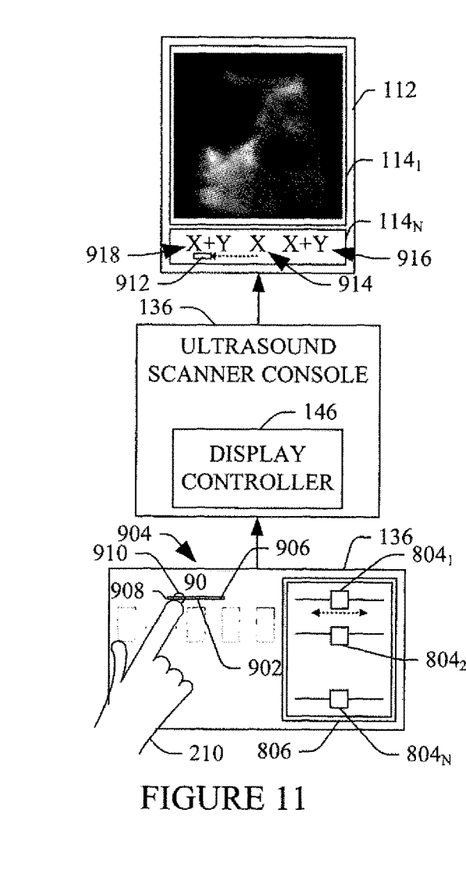

In FIG. 10, the user 210 moves the selector 910 by touching the selector 910 and sliding their finger across the touch screen user interface 122. Concurrently therewith, the selector 912 in the display region $114_N$ moves in coordination therewith, and the current values 904 and 914 increment by the same amount. In FIG. 11, the user moves the selector 910 in the opposite direction. Concurrently therewith, the selector 912 moves in coordination therewith, and the current values 904 and 914 decrement.

Figure 12:
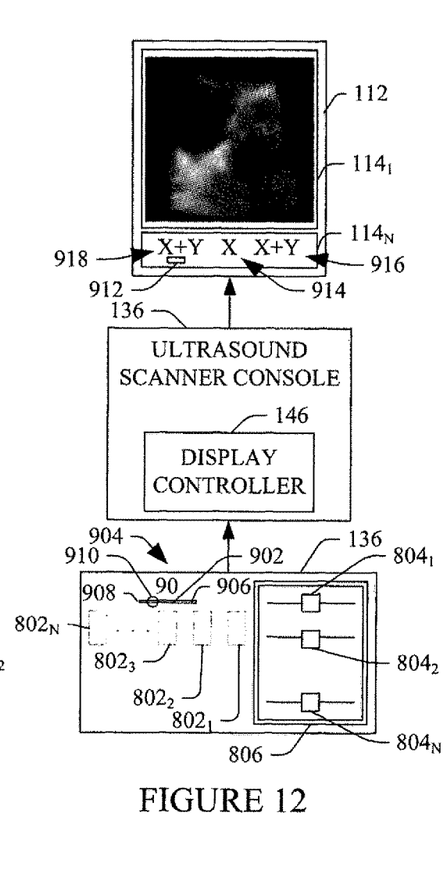
Figure 13:
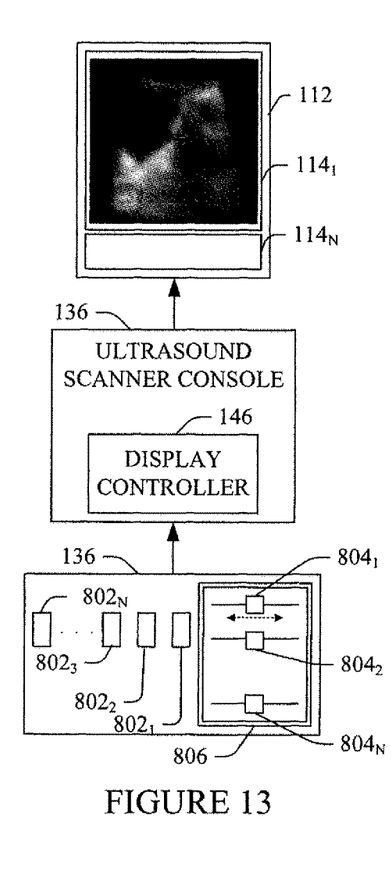

In FIG. 12, the user 210 ceases touching the touch screen user interface 122. In FIG. 13, after lapse of a pre-determined time duration in which the user 210 does not operate the control $802_3$, the value line 902, the current value 904, the end limits 906 and 908, the value selector 910, the value selector 912, the current value 914, and the minimum and maximum values limits 916 and 918, are removed from touch screen user interface 122 and the display region $114_2$ (or are no longer rendered), and the controls 802 and 804 transition to a state in which they are activatible.

Figure 14:
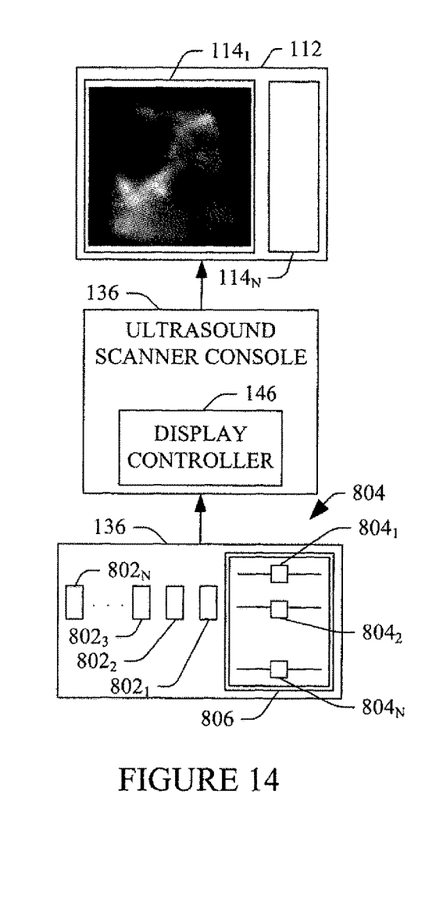
FIGS. 14-19 illustrate other example operation of the display controller in connection with another type of touch control.

FIGS. 14-19 illustrate other example operation of the display controller;

In FIG. 14, the display region $114_1$ is used to display an image. The display region $114_N$ is used to display a virtual control. The touchscreen user interface 122 includes the set of push controls $802_1$, $802_2$, $802_3$, ..., $802_N$ and the set of slide controls $804_1$, $804_2$, ..., $804_N$. All of the controls 802 and 804 are activatible.

Figure 15:
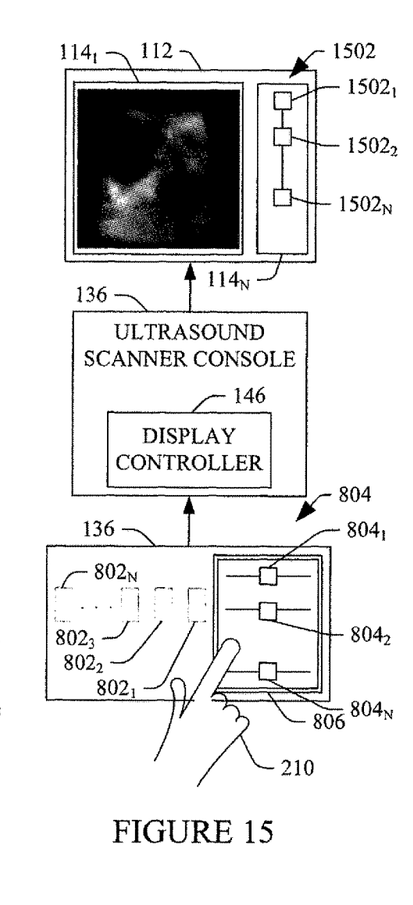

In FIG. 15, the user 210 actuates the set of slide controls 804 by pressing on the region 806. In this example, in response thereto, the controls 802 transition to a state in which they cannot be used, and a virtual slide control 1502, including virtual adjusters $1502_1$, $1502_2$, ... $1502_N$, is rendered in the display region $114_N$. In this example, the virtual adjuster $1502_1$, $1502_2$, ... $1502_N$ are each at a center position.

Figure 16:
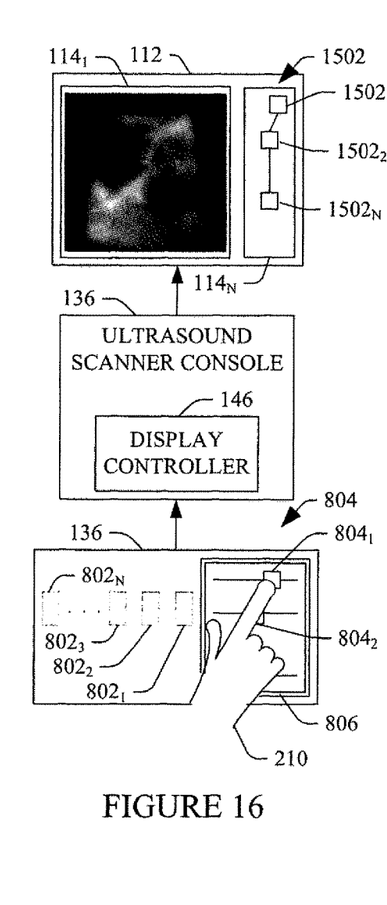
Figure 17:
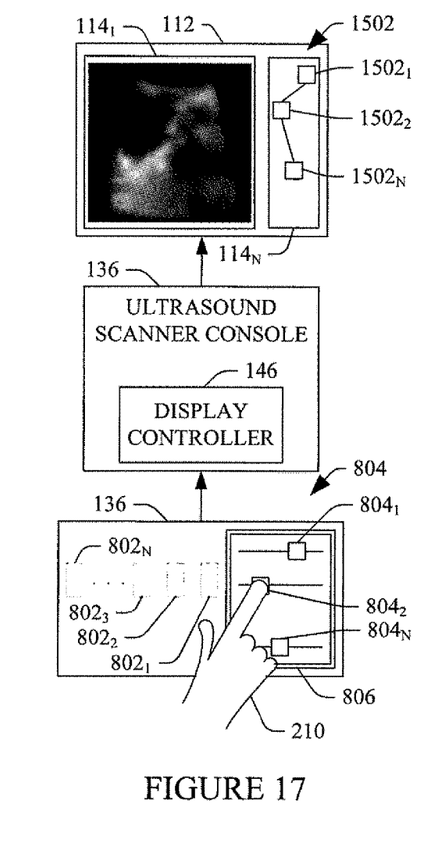

In FIG. 16, the user 210 moves the adjuster $804_1$ by touching the adjuster $804_1$ and sliding their finger across the touch screen user interface 122. Concurrently therewith, the virtual adjuster $1504_1$ in the display region $114_N$ moves in coordination therewith. In FIG. 17, the user 210 moves the adjuster $804_2$ by touching the adjuster $804_2$ and sliding their finger across the touchscreen user interface 122. Concurrently therewith, the virtual adjuster $1504_2$ in the display region $114_N$ moves in coordination therewith.

Figure 18:
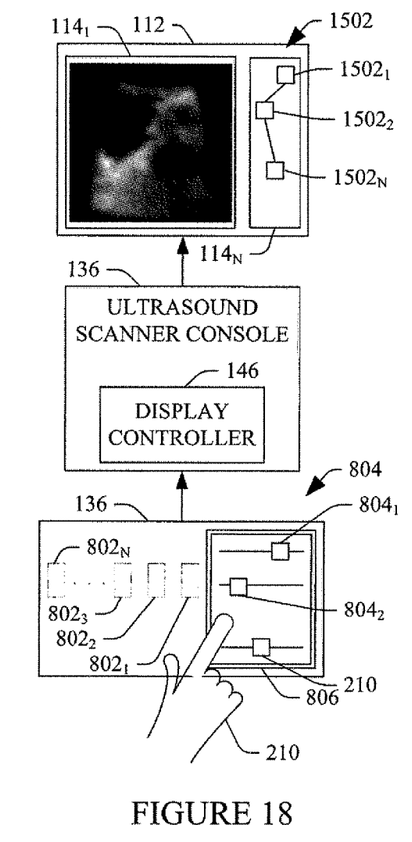
Figure 19:
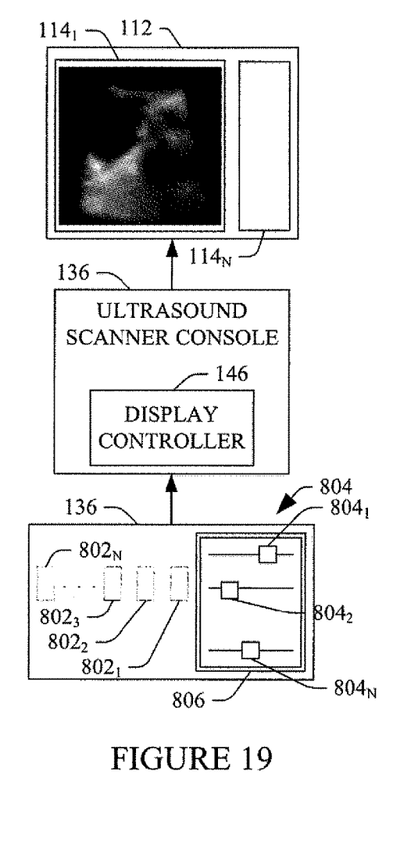

In FIG. 18, the user ceases touching the controls 804. In FIG. 19, after lapse of a pre-determined time duration in which the user does not operate any of the controls 804, the virtual control 1502 and the virtual adjusters $1502_1$, $1502_2$, ... $1502_N$ are removed from the display region $114_N$, and the controls 802 transition to a state in which they are activatible.

In FIGS. 8-13, the virtual controls are placed under the image. In FIGS. 14-19, the virtual controls are placed to one side of the image. In other embodiments, the virtual controls are place on top, on multiple sides of, within, etc. the image.

Figure 20:
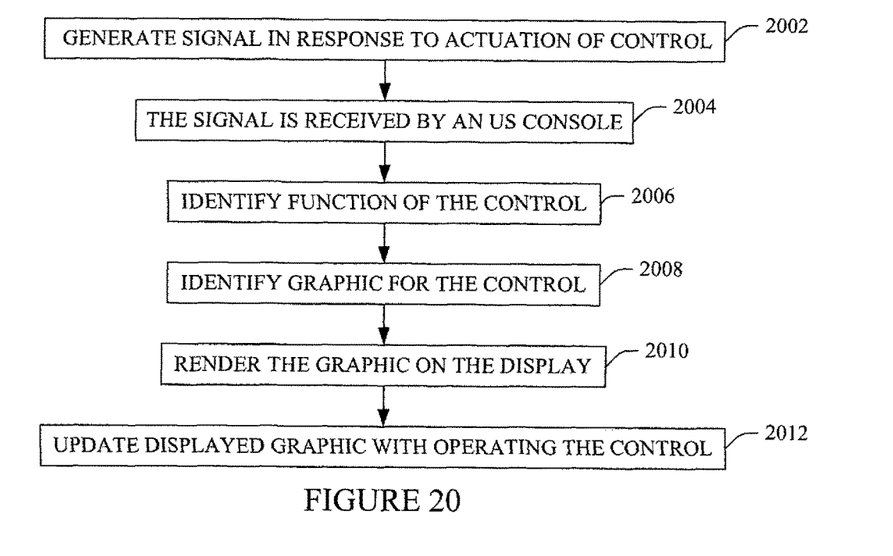
FIG. 20 illustrates example method for displaying a virtual control mimicking a touch control of the touch screen user interface.

FIG. 20 illustrates example method for displaying a virtual control mimicking a control of the touch screen user interface;

At 2002, a touchscreen control of a touchscreen user interface of an ultrasound scanning apparatus generates a signal in response to actuation of the touchscreen control.

At 2004, a display controller of an ultrasound console of the ultrasound scanning apparatus receives the signal.

At 2006, the display controller identifies the function assigned to the touchscreen control At 2008, the display controller identifies a visual graphic for the control, where the visual graphic mimics the appearance and/or operation of the control on the touchscreen user interface.

At 2010, the display controller renders the visual graphic on a display monitor.

At 2012, the display controller updates the displayed visual graphic in coordination with operation of the control on the touchscreen user interface, where the update mimics the appearance and/or operation of the control on the touchscreen user interface.

Figure 21:
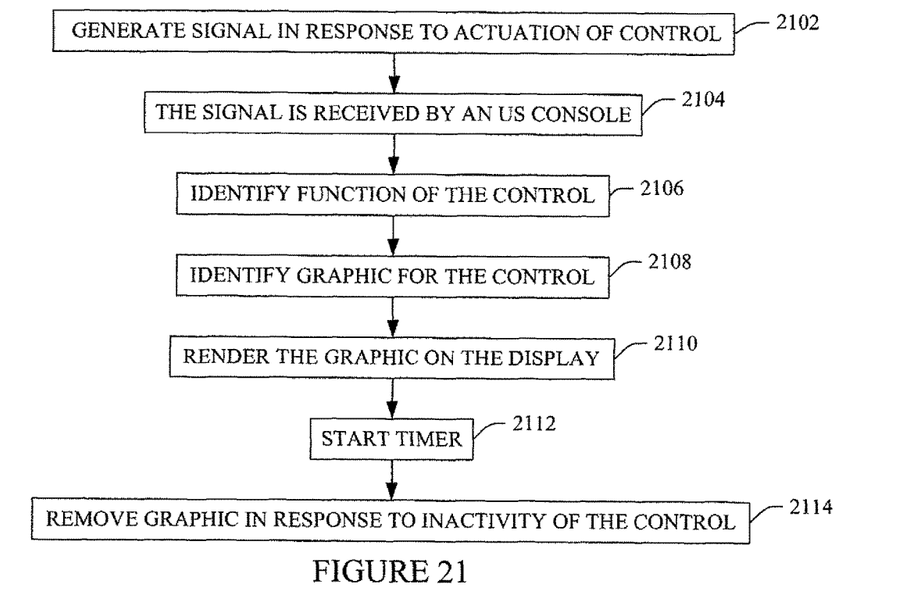
FIG. 21 illustrates example method for removing a displayed virtual control after lapse of a predetermined inactivity time.

FIG. 21 illustrates example method for removing a displayed virtual control after lapse of a predetermined inactivity time; and At 2102, a touchscreen control of a touchscreen user interface of an ultrasound scanning apparatus generates a signal in response to actuation of the touchscreen control.

At 2104, a display controller of an ultrasound console of the ultrasound scanning apparatus receives the signal.

At 2106, the display controller identifies the function assigned to the touchscreen control At 2108, the display controller identifies a visual graphic for the control, where the visual graphic mimics the appearance and/or operation of the control on the touchscreen user interface.

At 2110, the display controller renders the visual graphic on a display monitor.

At 2112, the display controller starts a timer.

At 2111, the display controller removes the graphic from the display monitor in response to lapse of a predetermine time duration in which a subsequent signal is not received from the control.

Figure 22:
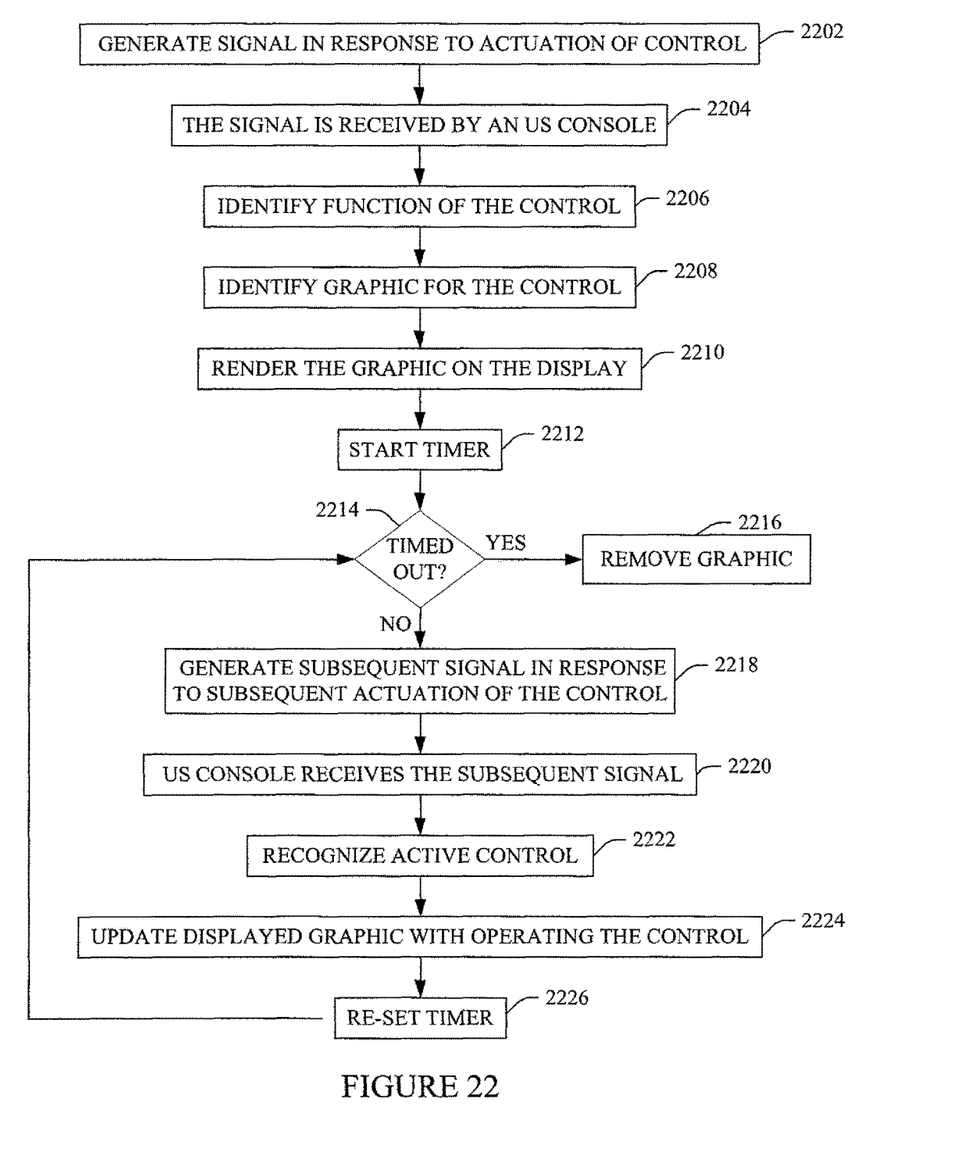
FIG. 22 illustrates example method for resetting a timer in response to subsequent use of the touch control of the touch screen user interface before lapse of the predetermined inactivity time.

FIG. 22 illustrates example method for resetting a timer in response to subsequent use of the control of the touch screen user interface.

At 2202, a touchscreen control of a touchscreen user interface of an ultrasound scanning apparatus generates a signal in response to actuation of the touchscreen control.

At 2204, a display controller of an ultrasound console of the ultrasound scanning apparatus receives the signal.

At 2206, the display controller identifies the function assigned to the touchscreen control At 2208, the display controller identifies a visual graphic for the control, where the visual graphic mimics the appearance and/or operation of the control on the touchscreen user interface.

At 2210, the display controller renders the visual graphic on a display monitor.

At 2212, a timer is started.

At 2214, it is determined if the timer time out.

If, the timer timed out, then at 2116, the display controller removes the graphic from the display monitor in response to lapse of a predetermine time duration in which a subsequent signal is not received from the control.

If the timer did not time out, then at 2218, the touchscreen control generates a subsequent signal in response to subsequent actuation of the touchscreen control.

At 2220, the display controller of the US console receives the subsequent signal.

At 2222, the display controller recognizes the control as the active control.

At 2224, the display controller updates the displayed visual graphic in coordination with operation of the control on the touchscreen user interface based on the subsequent signal At 2226, the timer is reset, and act 2214 is repeated.

At least a portion of the methods discussed herein may be implemented by way of computer readable instructions, encoded or embedded on computer readable storage medium (which excludes transitory medium), which, when executed by a computer processor(s), causes the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
    visually displaying, with a display controller of an ultrasound imaging system and in a display monitor, a first display region for displaying an ultrasound image, an ultrasound image in the first display region, and a second display region for a virtual control, initially not displaying any virtual control;
    receiving, at a console of the ultrasound imaging system, a first signal indicative of actuation of a touch control of a touch screen user interface of the ultrasound imaging system, wherein the touch control is one of a plurality of different touch controls of the ultrasound imaging system visually displayed on the touch screen user interface, and the touch control includes a value selector slide control;
    visually displaying, with the display controller and in response to the first signal, a virtual control in the second display region, the virtual control mimicking in appearance only the actuated touch control, including a graphic mimicking a current location of the value selector slide control displayed on the touch screen user interface;
    receiving, at the console, a second signal indicative of sliding, by a user, the value selector slide control across the touch screen user interface; and
    visually sliding, with the display controller and concurrently with receiving the second signal, the graphic across the second display region in coordination with the sliding of the slide control across the touch screen user interface.

2. The method of claim 1, further comprising:
    visually displaying, in response to the first signal and on the touch screen user interface, a value line, with minimum and maximum end limits, and the value selector on the value line at a location corresponding to a current value for the touch control between the minimum and maximum end limits.

3. The method of claim 1, further comprising:
    receiving, from the touch screen user interface, a third signal indicative of further sliding, by the user, of the slide control across the touch screen user interface; and
    further sliding the graphic across the second display region based on the third signal.

4. The method of claim 1, wherein the sliding of the slide control by the user increases or decreases a numeric value of a parameter controlled by the of the slide control, and further comprising:
    visually displaying, on the touch screen user interface, a current value of the parameter; and
    visually displaying, in second display region, the current value of the parameter along with the graphic.

5. The method of claim 1, wherein the sliding of the slide control by the user increases or decreases a numeric value of a parameter controlled by the of the slide control, and further comprising:
    visually displaying, at the touch screen user interface, first graphical indicia showing a change in the numeric value of the parameter; and
    visually displaying, in second display region, second graphical indicia showing the change in the numeric value of the parameter along with the graphic.

6. The method of claim 5, further comprising:
    starting a timer in response to receiving second signal.

7. The method of claim 6, further comprising:
    ceasing to visually display the virtual control, including the graphic, in second display region only in response to not receiving a subsequent signal from the touch screen user interface indicating subsequent actuation of the touch control for a pre-determined time duration, which is measured by the timer.

8. The method of claim 6, further comprising:
    re-starting the timer only in response to receiving a subsequent signal from the touch screen user interface indicating subsequent actuation of the touch control before lapse of the pre-determined time duration.

9. The method of claim 6, further comprising:
    re-starting the timer only in response to receiving a subsequent signal from the touch screen user interface before lapse of the pre-determined time duration, which is measured by the timer.

10. The method of claim 5, further comprising:
    ceasing to visually display the first graphical indicia on the touch screen user interface only in response to not receiving the subsequent signal from the touch screen user interface for the pre-determined time duration, which is measured by the timer.

11. An ultrasound imaging system, comprising:
    a touch screen user interface including a touch panel active region with one or more touch controls, wherein the touch controls includes at least one slide control;
    a display monitor including at least a first display region and a second display region, the first display region being configured for displaying an ultrasound image and the second display region being configured for displaying a virtual control; and
    an ultrasound scanner console including an echo processor and a display processor, wherein the ultrasound scanner console is configured for receiving a first signal indicative of an actuated touch control of the touch screen user interface, the display processor is configured for visually displaying, in response to the first signal, a graphic representation in the second display region mimicking in appearance only the actuated touch control, the graphic representation mimicking a current location of the value selector slide control displayed on the touch screen user interface, the ultrasound scanner console is further configured for receiving a second signal indicative of sliding the value selector slide control across the touch screen user interface, and the display processor is further configured for visually sliding the graphic representation across the second display region in coordination with the second signal indicative of the sliding of the value selector slide control across the touch screen user interface.

12. The ultrasound imaging system of claim 11, further comprising
- a memory that includes a visual graphic library with instructions for rendering a graphical representation for the one or more actuated touch controls, wherein the display processor is further configured to:
- sense the activation of one of the one or more touch controls in response to the first signal;
- identify the activated touch control of the one or more touch controls; and
- identify instructions from the memory for rendering the graphical representation for the one or more activated touch controls based on the identified activated touch control of the one or more touch controls and render the graphical representation in the second display regions,
- wherein the display processor visually displays, in response to the first signal, on the touch screen user interface, a value line, with minimum and maximum end limits, and a value selector on the value line being at a location corresponding to a current value for the touch control between the minimum and maximum end limits.

13. The ultrasound imaging system of claim 12, wherein the display processor senses an operation of the activated one of the one or more touch controls and, in response to sensing the operation, updates the graphical representation to reflect the operation.

14. The ultrasound imaging system of claim 13, wherein the operation is one of an increase or a decrease in a value of a variable, the graphical representation includes the value, and the display processor updates the visually displayed value based on the increase or decrease in the value of a variable to visually show a current value of the variable in the display region.

15. The ultrasound imaging system of claim 13, wherein the operation is one of an increase or a decrease in a value of a variable, the graphical representation includes non-numerical graphical indicia indicative of a relative value of the variable, and the display processor updates the non-numerical graphical indicia in coordination with the operation to visually reflect the increase or a decrease in the display region.

16. The ultrasound imaging system of claim 13, wherein the display processor, in response to lapse of a predetermined time interval in which the one of the one or more touch controls is not subsequently operated, removes the graphical representation from the one of the display regions.

17. The ultrasound imaging system of claim 11, wherein the display processor is further configured to start a timer in response to receiving the second signal at the ultrasound console and, in response to lapse of a predetermined time interval in which the one of the one or more touch controls is not subsequently activated, remove the graphical representation from the second display region and restart the timer only in response to receiving a subsequent signal from the touch screen interface before lapse of the predetermined time interval.

18. The ultrasound imaging system of claim 17, wherein the display controller is further configured to measure the predetermined time interval.

19. The ultrasound imaging system of claim 18, wherein the display processor re-starts the timer in response to receiving a signal indicating the one or more touch controls is subsequently operated.

20. A computer readable storage medium encoded with computer readable instructions which, when executed by a computer processor, cause the computer processor to:
- visually display in a display monitor a first display region for displaying an ultrasound image an ultrasound image in the first display region and a second display region for a virtual control initially not displaying any virtual control;
- receiving a first signal indicative of actuation of a touch control of a touch screen user interface of the ultrasound imaging system, wherein the touch control is one of a plurality of different touch controls of the ultrasound imaging system visually displayed on the touch screen user interface, and the touch control includes a value selector slide control;
- visually display in response to the first signal a virtual control in the second display region, the virtual control mimicking in appearance only the actuated touch control, including a graphic mimicking a current location of the value selector slide control displayed on the touch screen user interface;
- receive a second signal indicative of sliding by a user, the value selector slide control across the touch screen user interface; and
- visually slide concurrently with receiving the second signal, the graphic across the second display region in coordination with the sliding of the slide control across the touch screen user interface.

* * * * *